United States Patent
Collings et al.

(10) Patent No.: US 11,565,052 B2
(45) Date of Patent: Jan. 31, 2023

(54) RATCHET SYSTEMS FOR DRUG DELIVERY DEVICES

(71) Applicant: SANOFI, Paris (FR)

(72) Inventors: Ralph Donald Quentin Collings, Bristol (GB); James Robert Coop, Bristol (GB); James Anthony West, Bristol (GB); Stephen Francis Gilmore, Bristol (GB); Daniel David Higgins, Bristol (GB); Mark Digby Teucher, Bristol (GB); Stefan Blancke, Frankfurt am Main (DE)

(73) Assignee: Sanofi, Paris (FR)

( * ) Notice: Subject to any disclaimer, the term of this patent is extended or adjusted under 35 U.S.C. 154(b) by 243 days.

(21) Appl. No.: 16/766,204

(22) PCT Filed: Nov. 27, 2018

(86) PCT No.: PCT/EP2018/082640
§ 371 (c)(1),
(2) Date: May 21, 2020

(87) PCT Pub. No.: WO2019/102027
PCT Pub. Date: May 31, 2019

(65) Prior Publication Data
US 2020/0368446 A1    Nov. 26, 2020

(30) Foreign Application Priority Data
Nov. 27, 2017 (EP) .................... 17306640

(51) Int. Cl.
*A61M 5/315* (2006.01)
(52) U.S. Cl.
CPC .... *A61M 5/31526* (2013.01); *A61M 5/31553* (2013.01); *A61M 5/31583* (2013.01)

(58) Field of Classification Search
CPC .......... A61M 5/31526; A61M 5/31553; A61M 5/31583
See application file for complete search history.

(56) References Cited

U.S. PATENT DOCUMENTS

| | | | | |
|---|---|---|---|---|
| 2007/0129687 A1* | 6/2007 | Marshall | ............. | A61M 5/3155 604/207 |
| 2015/0148750 A1* | 5/2015 | Pedersen | ............. | A61M 5/3156 604/207 |

(Continued)

FOREIGN PATENT DOCUMENTS

| | | |
|---|---|---|
| JP | 2000-500680 | 1/2000 |
| JP | 2016-509903 | 4/2016 |
| JP | 2017-505177 | 2/2017 |

OTHER PUBLICATIONS

PCT International Search Report and Written Opinion in Application No. PCT/EP2018/082640, dated Jan. 15, 2019, 12 pages.

(Continued)

*Primary Examiner* — Dung T Ulsh
(74) *Attorney, Agent, or Firm* — Fish & Richardson P.C.

(57) ABSTRACT

A system comprises a first member, a second member, and a third member, wherein the first and second members are rotatable relative to the third member, wherein the first and second members are coupled to one another by a dead-angle follower coupling, wherein the dead-angle follower coupling is configured such that the first and second members are rotatable relative to one another, wherein the second and third members are rotationally coupled to one another by a switchable coupling mechanism, wherein the switchable coupling mechanism is switchable between two different states, a locked state and a non-locked state, wherein the maximum torque transferable between the second and third members via the switchable coupling mechanism in the locked state is greater than in the non-locked state, wherein (Continued)

the switchable coupling mechanism is in the locked state when the first member is in a locking position relative to the second member.

20 Claims, 7 Drawing Sheets

(56) References Cited

U.S. PATENT DOCUMENTS

| | | | |
|---|---|---|---|
| 2016/0228651 A1* | 8/2016 | Plambech | A61M 5/20 |
| 2016/0271332 A1* | 9/2016 | Bilton | A61M 5/31551 |
| 2017/0165431 A1* | 6/2017 | Markussen | A61M 5/31551 |
| 2017/0259006 A1 | 9/2017 | Avery et al. | |

OTHER PUBLICATIONS

PCT International Preliminary Report on Patentability in Application No. PCT/EP2018/082640, dated Jun. 2, 2020, 9 pages.

* cited by examiner

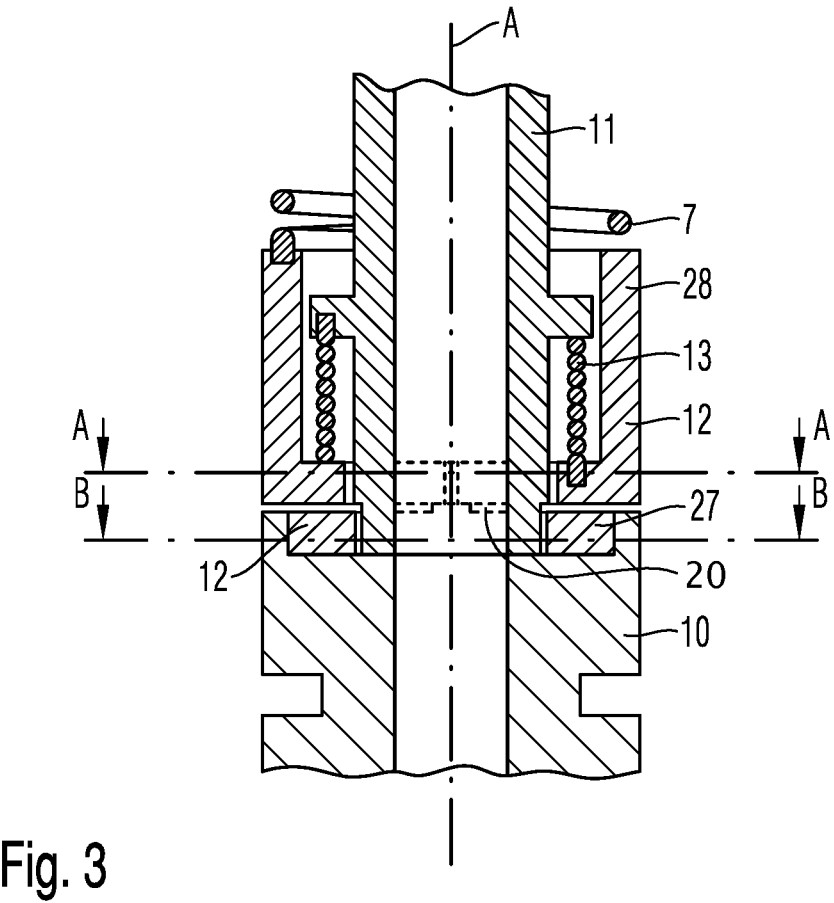
Fig. 3
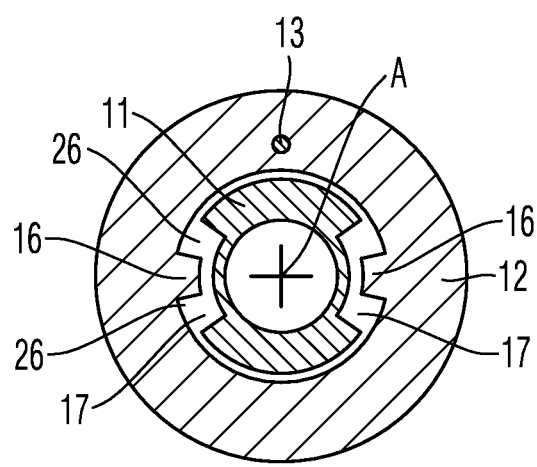
Fig. 4 (A-A)

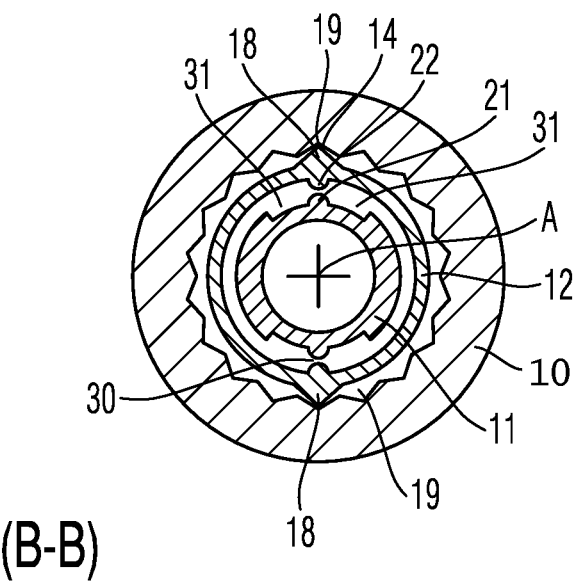
Fig. 5 (B-B)
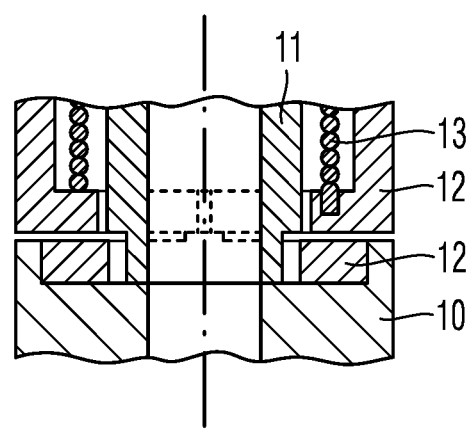
Fig. 6

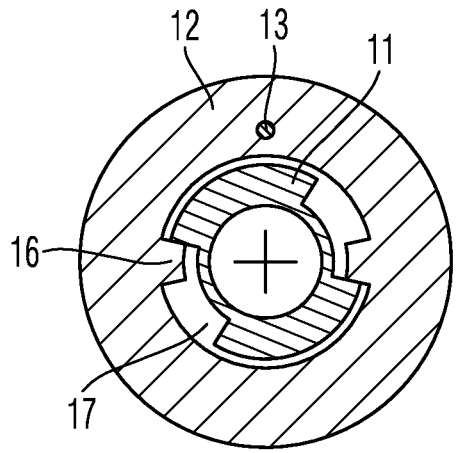
Fig. 7 (A-A)
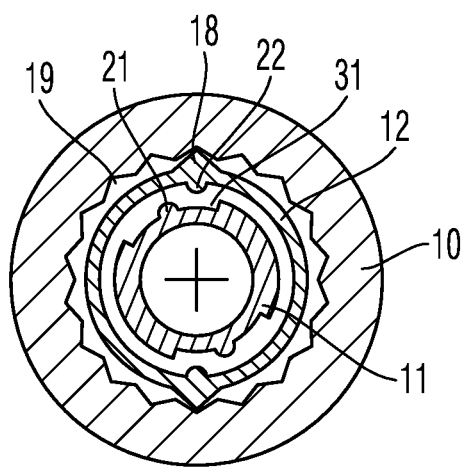
Fig. 8 (B-B)

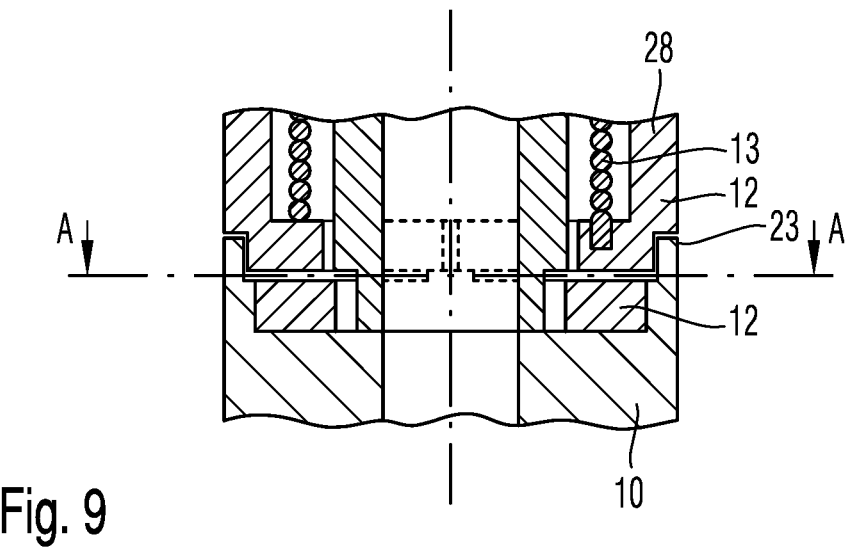
Fig. 9
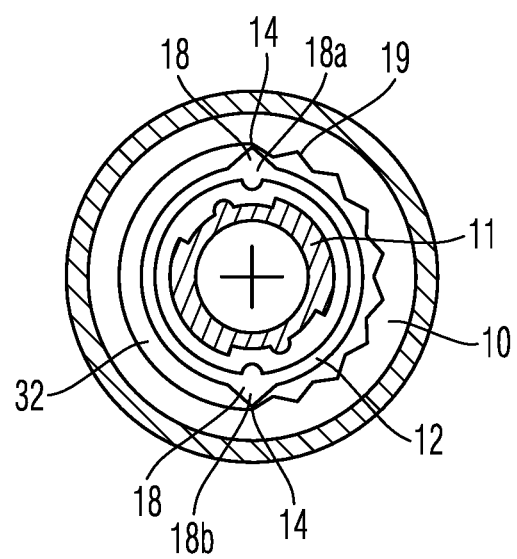
Fig. 10 (A-A)

RATCHET SYSTEMS FOR DRUG DELIVERY DEVICES

CROSS REFERENCE TO RELATED APPLICATIONS

The present application is the national stage entry of International Patent Application No. PCT/EP2018/082640, filed on Nov. 27, 2018, and claims priority to Application No. EP 17306640.8, filed on Nov. 27, 2017, the disclosures of which are incorporated herein by reference.

TECHNICAL FIELD

The present disclosure relates to a system for a drug delivery device.

SUMMARY

The system may be a ratchet system, particularly a rotational ratchet system. Still further, the present disclosure relates to a drug delivery device, which preferably comprises the system.

The present disclosure is particularly concerned with systems and concepts which are suitable to improve drug delivery devices particularly with respect to rotational couplings, e.g. their stability and/or their effective design.

Thus, it is an object of the present disclosure to provide systems which facilitate provision of an improved drug delivery device.

This object is achieved by the subject-matter of the independent claim, where advantageous embodiments and refinements may be subject to dependent claims. However, not only the claims but also the remaining disclosure may provide advantageous configurations of the systems disclosed herein. Particularly, the disclosed systems need not be restricted to the field of drug delivery devices but could also be applied in other technical fields. However, given the fact that precise operation of mechanisms of drug delivery devices, in particular the ones involved in setting and/or delivering doses of drug, is of the utmost importance, e.g. in view of the considerable risk which the user is exposed to in case of an improperly designed system, the disclosed systems are particularly suitable for drug delivery devices.

An aspect relates to a system, in particular to a system for a drug delivery device. The system may be a ratchet system. Another aspect relates to a drug delivery device comprising the system. Features disclosed above below, even if disclosed in conjunction with different embodiments or aspects, may be combined with one another. Furthermore, features disclosed in conjunction with other features are also regarded as being disclosed independently from one another.

In an embodiment, the system comprises a first member, a second member and/or a third member. Preferably, the system comprises at least two of the three members. The second and third member may, for example be coupled by a ratchet interface. Accordingly, these members may also be designated as ratchet members herein. References to the ratchet members may also be considered as referring to the second member and/or the third member and vice versa. The first member may be a locking member or a switching member. The function of this member is disclosed further below.

In an embodiment the first member and/or the second member is rotatable relative to the third member, preferably in one or two opposite rotational directions.

In an embodiment, the second member and the third member are rotationally coupled, preferably rotationally locked, to one another by a coupling mechanism, preferably a switchable coupling mechanism. The coupling mechanism between the second member and the third member may be configured to transfer a torque between the second member and the third member, preferably in both rotational directions. By means of the coupling mechanism, the third and the second member may be coupled to one another rotationally, in particular they may be rotationally locked, as long as the torque applied to the second and third member does not exceed a maximum torque which is transferable between the second member and the third member. In order to achieve the rotational locking between the second and the third member, angularly oriented faces of respective interface or ratchet features, e.g. teeth on the second and the third member, may abut or engage. The minimum force which is required to disengage the interface features, e.g. by relative movement, may define the maximum transferable torque. The switchable coupling mechanism may be switchable between two different states, a locked state and a non-locked state. The coupling between the second member and the third member may be configured to transfer a torque between the second member and the third member, preferably in both rotational directions, in the locked state as well as in the non-locked state.

In an embodiment, the system is configured such that the maximum torque transferable between the second member and the third member via the switchable coupling mechanism is greater in the locked state than in the non-locked state. Accordingly, in the locked state, the coupling may be more stable than in the non-locked state. The locked state may, for example be a safety state of the system such that the coupling may be more tolerant relative to mechanical vibrations or other impact forces acting on the coupling. Accordingly, in the locked state, for rotating the second member relative to the third member, a force or torque may be required which is greater, preferably considerably greater, than in the non-locked state. Relative rotation may even be prevented entirely. The maximum transferable force or torque, in the locked state, may be so great that the system has to be damaged to allow relative rotation between the second member and the third member. In the non-locked state, the coupling is releasable, e.g. by a user applied force, to rotate the second member relative to the third member.

In an embodiment, the rotational or angular position of the second member relative to the third member may be indicative for the size of a dose which has been set by a user in a dose setting operation. The set dose of drug may subsequently be delivered in a delivery or dispensing operation of the device.

In an embodiment, the second member may be a dose indication member, a dose follower or a number sleeve or coupled to one of these members. The second member may be provided with indicia which provide dose related information, e.g. information about the size of a dose which has been set in order to be dispensed from a drug delivery device.

In an embodiment, the first member and the second member are coupled to one another by a dead-angle follower coupling. The dead-angle follower coupling is expediently configured such that the first member and the second member are rotatable relative to one another but only within a limited angle range, preferably by less than or equal to one of the following angles in one or both rotational directions: 350°, 180°, 90°, 45°, 25°, 20°, 10°. Expediently, the first member is rotatable relative to the second member. The first member and the second member are rotatable relative to another preferably only within a limited angular range, e.g. as compared to the maximum angle by which the second member may be rotated relative to the third member. This angle may be defined by the maximum settable dose. The maximum angle may be greater than 360°, e.g. 720° or more.

In an embodiment, the switchable coupling mechanism is configured such that it is in the locked state when the first member is in a locking position, particularly an angular locking position, relative to the second member. The locking position may be within the limited angular range. The locking position may be chosen such that, starting from the locking position, the first member is rotatable relative to the second member by a first dead-angle in a first rotational direction to switch the coupling mechanism to the non-locked state and/or by a second dead-angle in a second rotational direction opposite to the first rotational direction to switch the coupling mechanism to the non-locked state. In this way, the non-locked state may be established in two different rotational directions. One of the rotational directions may be the one which is provided for incrementing a set dose, that is to say to increase the set dose to be delivered from the drug delivery device and the other direction may be the one for decrementing the set dose, i.e. decreasing the size of a dose to be delivered from the drug delivery device. When the first member has been rotated by the respective dead-angle relative to the second member the system is, preferably, in the non-locked state. In this state rotating the second member relative to the third member is easier, as the maximum transferable torque is lowered in the non-locked state.

In an embodiment, the first member is a dose setting member or be coupled to the dose setting member. The dose setting member may be a member which is provided as a user interface in the drug delivery device. That is to say, the dose setting member may be manipulated by a user for setting a dose. If, when a dose has been set, the user discovers that the size of the set dose is wrong for the desired purpose, the dose can be decreased or increased by rotating the dose setting member in the appropriate direction.

In an embodiment, the system is configured such that, after the relative rotation by the first dead-angle has been performed starting from the locking position, the first member and the second member are rotationally locked in the first rotational direction. Rotation of the first member relative to the second member in the opposite rotational direction towards the locking position, however, is allowed.

In an embodiment, the system is configured such that, after the relative rotation by the second dead-angle has been performed starting from the locking position, the second member and the first member are rotationally locked in the second rotational direction. Rotation of the first member relative to the second member in the opposite rotational direction towards the locking position, however, is allowed.

That is to say, the dead-angle follower coupling may provide a coupling, which permits rotation by a dead-angle in a particular rotational direction and, after this rotation has been performed, the first and second member are rotationally locked in that particular direction. Accordingly, when the first member is rotated away from the locking position, it may, at first, be rotated relative to the second member in that direction and, afterwards, it carries the second member with it such that the second member is rotated in the same direction as the first member relative to the third member.

In an embodiment, the first and second dead-angles are different or equal.

In an embodiment, the second member and the third member are coupled to one another by a mechanical interface, e.g. a ratchet interface. The mechanical interface may be configured to define, preferably stable, relative angular positions between the second member and the third member. The relative angular positions may be defined such that the second member can be rotated relative to the third member, preferably only, in whole-number multiples of a unit increment. The unit increment is expediently constant. It may be set by the design of the mechanical interface. Thus, the second member, starting from an initial angular position, has to be rotated relative to the third member at least by an angle corresponding to the unit increment to obtain the adjacent relative angular position. Otherwise, the relative position after the rotation has been finished will not be stable and the second member is expediently returned to the initial position.

In an embodiment, the mechanical interface between the second and the third member may be formed by means of interface features, e.g. one or more teeth, on the second member engaging and/or cooperating with interface features, e.g. one or more teeth, of the third member, particularly in each relative angular position defined by the interface. The unit increment may be defined by the distance between two adjacent interface features on the same member. The unit increment may define the minimum dose which is settable by the system. Particularly, the mechanical interface may be formed by means of at least one interface feature of the second member and at least one interface feature of the third member which engage one another in each relative angular position.

In an embodiment, the respective interface features are ratchet features. Thus, features disclosed herein above and below with respect to interface features do also apply for ratchet features and vice versa.

In an embodiment, the mechanical interface is a radial interface. Particularly, in order to rotate the second member relative to the third member or vice versa, a radial displacement of one of the interface features with respect to the other one of the interface features is required expediently.

In an embodiment, the first dead-angle and/or the second dead-angle is less than the angle corresponding to one unit increment. Accordingly, in order to switch the mechanism from the locked state to the non-locked state, the user has to rotate the first member less than one unit increment. Therefore, the user almost does not notice that the second member does not immediately follow the user initiated rotation of the first member.

In an embodiment, the angle corresponding to one unit increment is less than 30°. The angle corresponding to one unit increment may be greater than 4°, preferably greater than 10°. For example, the angle corresponding to one unit increment may be 20°.

In an embodiment, the mechanical interface rotationally locks the second and the third member to one another, expediently in one or both rotational directions. The strength of the mechanical lock, that is to say the torque which can be transferred between the second and third member may be switched according to the position of the first member relative to the second member. It may be greater in the locked state than in the non-locked state.

In an embodiment, the switchable coupling mechanism comprises the mechanical interface and a locking feature associated with the first member or provided on the first member. The locking feature may be arranged to prevent disengagement of the interface features which rotationally lock the second and third member in the locking position.

When the first member has been rotated by the dead-angle, i.e. in the non-locked state, disengagement of the interface features is allowed, preferably only if the torque exceeds the maximum transferable torque in the non-locked state.

In an embodiment, when the first member is in the locking position, the locking feature is arranged to limit or to prevent a relative movement, preferably a relative radial movement, between the interface features forming the mechanical interface, expediently to an extent such that disengagement of the interface features is prevented. Thus, when in the locking position, the second and the third member may be reliably kept in the relative position required for rotationally locking the second member and the third member to one another.

In an embodiment, when it is in the locking position, the locking feature may be arranged to allow a limited, e.g. radial, movement between the interface features, but only to an extent which is insufficient to rotate the second member by one unit increment to the adjacent angular position. Thus, the locking feature may be free of any rotational or torque load present in the system. The load may be reacted entirely by the mechanical interface. The limited radial movement may be defined by a clearance between the locking feature and the second member.

In an embodiment, the mechanical interface is strong enough to provide stable relative angular positions between the second and the third member and can react all the internal forces occurring during operation of the system, e.g. in a drug delivery device. However, in case of additional external forces such as impact forces, which may occur when a drug delivery device is dropped on the floor or similar irregular forces, the locking feature may be arranged to prevent the disengagement of the interface features.

In an embodiment, the system comprises an energy storage member, such as a spring, for example a torsion spring. The second member may be coupled to the energy storage member. Rotation of the second member in a first rotational direction relative to the third member, e.g. an incrementing direction, may increase the energy stored in the energy storage member. The energy stored in the energy storage member may tend to rotate the second member in a second rotational direction, e.g. a decrementing direction, opposite to the first rotational direction. To put it in different words, the system may be a wind-up system, where energy stored in an energy storage member is increased by rotating the second member in the first direction. This energy may be used to drive rotational movement of the second member in the second rotational direction, e.g. a decrementing direction, when the second member is released, e.g. by releasing the mechanical interface. The stored energy may be used to drive a dispensing movement in a drug delivery device, for example. If the stored energy should be decreased in a controlled manner, the second member may be rotated in the decrementing direction relative to the third member via the first member.

In an embodiment, the mechanical interface between the second member and the third member is capable of reacting the torque transferred to the second member from the energy storage member in the non-locked state. Thus rotation of the second member may be prevented by the mechanical interface regardless of the position of the first member, unless the torque transferred to the second member via the first member, e.g. by the user, assists in rotating the second member relative to the third member.

In other words, the mechanical interface established between the second member and the third member is expediently strong enough to withstand the torque which is provided by the energy stored in the energy storage member and tends to rotate the second member relative to the third member. However, as will be immediately apparent, the more energy is stored in the energy storage member, the less stable the interface between the second and the third member becomes, such that the additional force or torque which is required to release the interface and rotate the second member relative to the third member in the decrementing direction is reduced. Thus, providing the switchable coupling mechanism which prevents an unintentional release of the mechanical interface, e.g. in case of an external impact force, regardless of the energy stored in the energy storage member is advantageous. For example, if a dose has been set in a drug delivery device and the device is accidentally dropped on the floor, a device without such a switchable coupling mechanism would likely deliver at least a partial dose or the entire dose which has been previously set. This can be avoided by providing the switchable coupling mechanism.

In an embodiment, the maximum torque transferable between the second and the third member via the mechanical interface may be different in different rotational directions, particularly in the non-locked state. Thus, the mechanical interface may be asymmetric. Expediently the maximum torque is greater in that direction in which the energy stored in the energy storage member tends to rotate the second member. This may be achieved by an asymmetric mechanical interface, for example by ratchet features, e.g. teeth, having differently sloped flanks or angular faces. Alternatively, the mechanical interface may be symmetric, that is to say, the maximum transferable torque may be equal in both rotational directions.

In an embodiment, the energy stored in the energy storage member assists a decrementing movement or rotation of the second member relative to the third member. That is to say, for the user it may seem easier to decrement the dose than to increment the dose. This may hold if the mechanical interface itself is symmetric or even if it is asymmetric.

In an embodiment, the system comprises a biasing mechanism. The biasing mechanism may be configured to exert a force which tends to maintain or move the first member into the locking position relative to the second member, particularly when the first member has been displaced away from the locking member such as in the first rotational direction and/or in the second rotational direction. Accordingly, the locking position may be the regular position which the first member has relative to the second member. Therefore, unless the system is manipulated by the user such as for rotating the second member relative to the third member in either rotational direction, the system is in the locked state. The biasing mechanism may be realized by one or a plurality of springs which tend to maintain or move the first member into the locking position relative to the second member when the first member has been rotated relative to the second member.

In an embodiment, the system is configured such that the rotational coupling provided by the switchable coupling mechanism and/or the mechanical interface between the second member and the third member may be released, preferably by a relative, e.g. axial, movement between the second member and the third member. This movement may be a movement which is, for example, required in order to initiate or trigger a dispensing action in the drug delivery device such that the set dose of drug which has been previously dialed or set is dispensed, for example by using the energy stored in the energy storage member. When the coupling or interface is released, the second member may rotate freely.

In an embodiment, when the rotational coupling has been released, the second and the third member are rotationally locked to one another, e.g. by a splined connection, such that rotational movement of the second member is transferred to the third member. Thus, by means of the axial movement, the third member may be rotationally decoupled form a fourth member, e.g. a housing, of the system or the drug delivery device and rotationally locked to the second member. The third member may, therefore have the function of rotationally locking the second member in a first axial configuration and in a second axial configuration, e.g. when the third member has been axially displaced relative to the second member and/or the fourth member, be a member driven by the second member, e.g. via energy stored in the energy storage member.

In an embodiment, the second member (first ratchet member) comprises a plurality of second member interface features (first ratchet features) which are distributed circumferentially or angularly, where, preferably, the angular distance between at least two adjacent second member interface features is greater than the angle corresponding to one unit increment. Additionally or alternatively, the third member (second ratchet member) comprises a plurality of third member interface features (second ratchet features) which are distributed circumferentially or angularly where, preferably, the angular distance between at least two adjacent third member interface features is greater than the angle corresponding to one unit increment. The system is preferably configured such that, in any relative angular position defined by the mechanical interface, an angular face of at least one, preferably of only one, third member interface feature interacts with an angular face of at least one, preferably of only one, second member interface feature, in particular to prevent relative rotational movement between the second and the third member in the first rotational direction and/or in the second rotational direction. One angular face of a second member interface feature which faces in a first rotational direction may interact with one angular face of a third member interface feature which faces in a second rotational direction opposite to the first direction. Another angular face of a second member interface feature which faces in the second rotational direction may interact with one angular face of a third member interface feature which faces in the first rotational direction. The angular faces may be part of the same second member interface features or of different second interface features.

Thus, although the respective interface features may be distributed in the angular or circumferential direction in a (regular or irregular) pattern which has at least one or more than one sections, where adjacent interface features on the same member have an angular separation or distance greater than the angle corresponding to one unit increment, the mechanical interface may still define relative angular positions between the members in whole-number multiples of one unit increment. The section between two adjacent interface features, which has a greater separation may provide a pass through region through which a feature of an additional element can be guided during assembling, e.g. of a drug delivery device.

In an embodiment, the respective interface feature is radially oriented. In other words, the interface features may have a radial free end.

In an embodiment, in the respective angular or rotational direction, the interface features may be delimited by an angular face or surface.

In an embodiment, all of the angular faces which delimit the second member interface features in a first rotational or angular direction form a first set of angular faces of the second member. All of the angular faces which delimit the second member interface features in the second rotational or angular direction opposite to the first rotational or angular direction may form a second set of angular faces of the second member. The first and the second set do not overlap.

In an embodiment, all of the angular faces which delimit the third member interface features in a first rotational or angular direction form a first set of angular faces of the third member. All of the angular faces which delimit the third member interface features in the second rotational or angular direction opposite to the first rotational or angular direction may form a second set of angular faces of the third member. The first and the second set do not overlap.

In an embodiment, in each relative angular position defined by the mechanical interface, only a subset, i.e. a true subset, of the angular faces of the first set of angular faces of the second member is arranged to cooperate with only a subset, i.e. a true subset, of the angular faces of the second set of angular faces of the third member. The respective subset may have just one element. Consequently, in each position, only one pair of angular faces may form the mechanical interface in one rotational direction.

In an embodiment, in each relative angular position defined by the mechanical interface, only a subset, i.e. a true subset, of the angular faces of the second set of angular faces of the second member is arranged to cooperate with only a subset, i.e. a true subset, of the angular faces of the first set of angular faces of the third member. The respective subset may have just one element. Consequently, in each position, only one pair of angular faces may form the mechanical interface in the other rotational direction.

Thus, in summary, in each rotational direction, only one pair of angular faces may form the mechanical interface.

The angular faces of the different sets which are arranged to cooperate with one another may abut, be arranged to abut, and/or be arranged in an angular distance corresponding to less than one unit increment, e.g. less than 0.1 unit increment.

In an embodiment, the second member interface features and/or the third member interface features are grouped into one or more groups, where, in each group, adjacent interface features are separated by an angle corresponding to one unit increment. It is preferred that only one of the second member interface features and the third member interface features are grouped. The other interface features may be individual interface features adapted to engage with the interface features in the one or more groups. If there is more than one group, the angular extension of the groups is expediently constant. The groups may be uniformly distributed in the angular or circumferential direction.

In an embodiment, in each relative angular position defined by the mechanical interface, at least two or exactly two angular faces, which face in different angular or rotational directions and delimit one of the interface features which are configured to interact with the one or more groups, are arranged angularly outside of the one or more groups and/or do not engage an interface feature of the one or more groups. The two angular faces may be part of the same interaction feature or of different interaction features. In one relative position, the two angular faces may be part of or delimit the same interaction feature. In another relative angular position, the two angular faces may be part of or delimit different interaction features.

In an embodiment, in each relative angular position defined by the mechanical interface, at least two or exactly two angular faces, which face in different angular or rotational directions and delimit one of the interface features which are configured to interact with the one or more groups, do engage an interface feature of the one or more groups. The two angular faces may be part of the same interaction feature or of different interaction features. In one relative position, the two angular faces may be part of or delimit the same interaction feature. In another relative angular position, the two angular faces may be part of or delimit different interaction features.

In an embodiment, two adjacent groups are separated by an angle corresponding to more than one unit increment. The distance between two, preferably arbitrary adjacent groups is preferably defined by whole-number multiples of one unit increment. This helps to ensure that, despite of the separation of the groups, the mechanical interface still defines angular positions in whole number multiples of the unit increment.

In an embodiment, if there is more than one group, the angular extensions of the groups are equal and/or the distances between two adjacent groups are equal. The groups may be formed alike and/or be uniformly distributed.

In an embodiment, the sum of the angular extensions of all groups is greater than or equal to 180°.

In an embodiment, the sum of the angular extensions of all gaps between groups is less than or equal to 180°.

In an embodiment, the angular distance between two, preferably arbitrary, adjacent interface features which are adapted to cooperate with the interface features in the one or more groups is greater than or equal to the angular extension of one of the groups.

In an embodiment, the minimum angular distance between two, preferably arbitrary, adjacent interface features which are adapted to cooperate with the interface features in the one or more groups is defined by, e.g. equal to, the angular extension of one of the groups, preferably the smallest angular extension.

It should be noted that the system with the switchable coupling and the ratchet system between the third member and second member are disclosed independently from one another but may be applied in combination, of course.

The terms "angular" (or azimuthal), "axial" and "radial" as used herein may be understood as referring to a defined axis of the system, e.g. a main longitudinal axis, a rotation axis around which the first, second and/or third member rotate, and/or an axis around which the first, second and/or third member are disposed, e.g. concentrically.

In an embodiment, the drug delivery device comprises the system disclosed herein. In addition, the device may comprise a reservoir holding the liquid drug to be dispensed from the device. The device may comprise a piston rod, which is arranged to drive the dispensing movement. The first member of the system may be a dose setting or correcting member. The second member may be a dose indication member or dose follower. The third member may be a housing, preferably an exterior housing of the drug delivery device, a member of the drug delivery device permanently rotationally locked to the housing or a member of the drug delivery device which is rotationally locked relative to the housing during dose setting and/or correcting but rotatable relative to the housing during dose delivery, e.g. a drive member. The drive member may be, preferably immediately, coupled to a piston rod of the drug delivery device. The drive member may be rotationally locked to the second member during dose delivery in order to transfer driving force from the energy storage member via the dose indication member or dose follower to the drive member. The rotational lock may be established when the mechanical interface is released.

In a particularly advantageous embodiment, the system, comprises a first member, a second member, and a third member, wherein the first member and the second member are rotatable relative to the third member, wherein the first member and the second member are coupled to one another by a dead-angle follower coupling, wherein the dead-angle follower coupling is configured such that the first member and the second member are rotatable relative to one another but only within a limited angular range, wherein the second member and the third member are rotationally coupled to one another by a switchable coupling mechanism, wherein the switchable coupling mechanism is switchable between two different states, a locked state and a non-locked state, wherein the maximum torque transferable between the second member and the third member via the switchable coupling mechanism in the locked state is greater than in the non-locked state, wherein the switchable coupling mechanism is configured such that the switchable coupling mechanism is in the locked state when the first member is in a locking position relative to the second member, the locking position being within the limited angular range, wherein the locking position is chosen such that, starting from the locking position, the first member is rotatable relative to the second member by a first dead-angle in a first rotational direction to switch the coupling mechanism to the non-locked state and by a second dead-angle in a second rotational direction opposite to the first rotational direction to switch the coupling mechanism to the non-locked state.

As detailed above, this system facilitates provision of drug delivery devices having improved user safety.

In a particularly advantageous embodiment, a ratchet system comprises a first ratchet member and a second ratchet member which are rotatable relative to one another, in particular with respect to an axis of rotation, wherein the ratchet members are coupled by a ratchet interface, the ratchet interface being formed by engagement of first ratchet features provided on one of the ratchet members and second ratchet features provided on the other one of the ratchet members, wherein the ratchet interface is configured to define stable relative angular positions between the two ratchet members in whole-number multiples of a unit increment, wherein two adjacent first ratchet features are separated by an angle greater than the angle corresponding to one unit increment, and wherein two adjacent second ratchet features are separated by an angle greater than the angle corresponding to one unit increment. Preferably, only one angular face of all of the first ratchet features is arranged to cooperate with only one angular face of all of the second ratchet features to define the stable position in each stable position. This preferably holds in both opposite rotational directions. The angle separating adjacent ratchet features may be defined by the unit increment, e.g. correspond to two unit increments or more than two unit increments.

In the regions with larger distances, features of other elements can be guided axially across the region with the ratchet features thereby passing through the region where no ratchet features are provided during assembly, e.g. of a drug delivery device.

Further features, advantages and advantageous refinements of the present disclosure will become apparent from the following description of the exemplary embodiments in conjunction with the drawings.

BRIEF DESCRIPTION OF THE FIGURES

FIGS. 2 to 8 schematically illustrate one implementation of a system, particularly a system comprising a switchable coupling mechanism, on the basis of various different views.

FIGS. 9 to 12 schematically illustrate another implementation of a system, particularly a ratchet system, on the basis of various different views, which could be used in the implementation shown in FIGS. 2 to 8 or separately. Therein, FIG. 10 and FIGS. 11 and 12 illustrate different embodiments of the implementation.

In the drawings, identical elements, identically acting elements and elements of the same kind may be identified using the same reference numerals.

DETAILED DESCRIPTION

Figure 1:
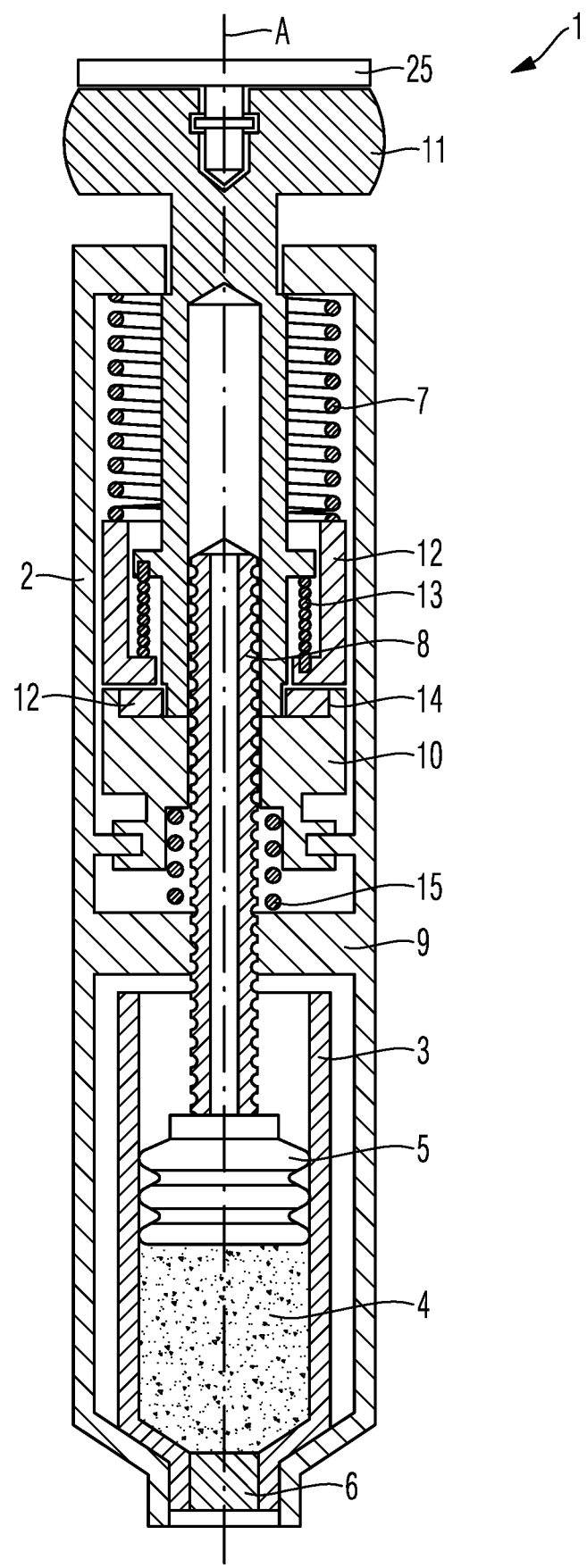
FIG. 1 shows a schematic sectional view of an embodiment of a drug delivery device.

FIG. 1 illustrates an embodiment of a drug delivery device 1 on the basis of a schematic sectional view. The drug delivery device 1 may be a pen-type device and/or an injection device. The drug delivery device is expediently configured to dispense drug from a reservoir retaining the drug, preferably via a needle. For example, the drug delivery device may be configured to subcutaneously deliver drug to a patient via a needle.

In the depicted embodiment, the drug delivery device comprises a housing 2. The housing 2 may have a general cylindrical shape which might resemble the shape of a fountain pen. The housing 2 retains the reservoir 3, e.g. a cartridge, such as a rigid cartridge, like a glass cartridge, which retains the drug, preferably a liquid drug. The depicted housing 2 is of a single-part construction. However, it is immediately apparent, that the housing may comprise separate parts which are releasably or permanently secured to one another. Thus, multi-part housings may be possible as well.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The reservoir 3 has a distal end and a proximal end. Drug leaves the devices 1 via the distal end of the reservoir 3. On the side of the proximal end the reservoir may be sealingly closed by a movable bung or stopper 5. When the bung 5 is moved towards an open (distal) end of the reservoir, drug 4 is dispensed from the reservoir 3, provided that fluid communication is established between the interior of the reservoir and the environment, e.g. by a needle piercing through a sealing member or septum 6, which may close the open end of the reservoir 3. The reservoir 3 is retained in a reservoir retaining section of the housing. If the housing 2 is of multi-part construction, the reservoir retaining section may be, permanently or releasably, attached to the remainder of the housing. If the reservoir retaining section or member is releasably secured to the remainder of the housing, the reservoir may be exchanged after the last dose of drug has been delivered from the reservoir with a new reservoir. For replacing the reservoir, the retaining member may be detached from the housing, the reservoir may be removed from the retaining member or holder and replaced with a new reservoir which is introduced into the retaining member and, thereafter, the retaining member is connected again to the remainder of the housing.

Further, within the housing 2, a dose setting and/or dose delivery mechanism is retained. This mechanism is expediently provided to set the size of a dose which may subsequently be delivered. Expediently, the mechanism is designed such that a dose once it has been set can be altered, e.g. increased or decreased, again. Accordingly, a dose correction function may be implemented in the dose setting mechanism. The drive mechanism may be a drive mechanism, which utilizes energy stored in an energy storage member 7. Via the drive mechanism, the force may be transferred within the device to the bung 5. The force may originate from energy released from the energy storage member.

The term "distal" as used herein designates that end of an element of the device or the device, which is to be arranged closest to the dispensing end of the device. The distal direction is a direction towards the dispensing end. As opposed thereto, the term "proximal" designates that end of an element of the device or the device, which is to be arranged closest to the dispensing end of the device. The proximal direction is a direction away from the dispensing end.

The energy storage member 7 may be a spring, e.g. a torsion spring. In order to dispense drug 4 from the reservoir 3, the energy stored in the energy storage member 7 may be released. During dose setting, energy for dispensing the set dose may be stored in the storage member 7, e.g. by the user. This energy may be used to drive a piston rod 8 of drive mechanism, which is movably retained in the housing 2 in the distal direction. Thereby, the piston rod 8 may advance the bung 5 distally within the reservoir. In the depicted embodiment, the piston rod 8 is threadedly engaged with a nut section or member 9 of the drug delivery device. Although, the nut section 9 is depicted as an integral section of the housing 2, a separate member may be provided for this purpose, which preferably is rotationally and axially locked relative to the housing at least during dose setting and dose dispensing. On account of threaded engagement rotation of the piston rod 8 relative to the housing 2 results in axial displacement of the piston rod relative to the housing. Rotation in one rotational direction may result in distal movement and rotation in the opposite direction may result in proximal movement of the piston rod 8.

The drug delivery device 1 further comprises a drive member 10. The drive member 10 is coupled to the piston rod, preferably immediately coupled. In the exemplary embodiment, the drive member 10 is coupled to the piston rod via a splined connection or engagement. That is to say, the drive member 10 and the piston rod 8 are coupled to be co-rotatable only. Relative rotation between the drive member 10 and the piston rod 8 is not permitted. Accordingly, rotation of the drive member 10 results in rotation of the piston rod which, consequently results in displacement of the bung 5 in the distal direction. Of course, other configurations are also possible to drive the piston rod. For example, the piston rod may be splined relative to the housing and threadedly engaged with the drive member.

For setting a dose and, preferably, for correcting a set dose, the drug delivery device 1 comprises a dose setting member 11. The dose setting member 11 is designed to be rotatable relative to the housing 2. It may be axially constrained relative to the housing during dose setting and/or in the proximal direction. Limited axial movement may be permitted in the distal direction, e.g. to trigger or initiate a dispensing action. Rotation of the dose setting member 11 in one direction may increase the size of the dose to be delivered, expediently in an incremented fashion where the dose may be increased only in multiples of a unit increment. Rotation in the opposite direction may decrease the size of the dose to be delivered, when starting from a non-zero dose which has been set previously. The drive member 10 is expediently rotationally locked relative to the housing during dose setting. Movement of the piston rod 8 during dose setting can be avoided in this way. For delivering the dose, the rotational lock may be released, preferably by an axial movement of the drive member relative to the housing 2.

The device 1 further comprises a button 25. The button 25 is preferably axially secured to the dose setting member 11, where relative rotation between button 25 and dose setting member 11 is permitted. The button 25 may form the user interface for initiating a dispensing action by pressing the button 25, e.g. distally. For dose setting, the user may grip the dose setting member at the side surface and rotate the dose setting member until dose dose of a desired size has been set.

The device further comprises a movable member 12 or dose follower. The movable member 12 is preferably coupled to the energy storage member 7 and rotatable with respect to the housing. Rotation in one direction, preferably the one for increasing the size of a set dose, i.e. the incrementing direction, increases the energy stored in the storage member. Rotation in the opposite direction, preferably the one for decreasing the size of a set dose, i.e. the decrementing direction, expediently decreases the energy stored in the storage member. One end of the energy storage member may be fixed to the housing 2 and the other end may be fixed to the movable member 12. Consequently, the energy stored in the storage member 7 tends to rotate the movable member 12 in the decrementing direction. This rotation may be used to drive the dispensing movement.

The dose setting member 11 is rotationally coupled to the movable member 12 or dose follower. Thus, the movable member may follow rotation of the dose setting member in two opposite rotational directions, the incrementing direction and the decrementing direction. The coupling between the dose setting member and the movable member 12, which is configured to permit only limited relative rotational movement between the dose setting member 11 and the movable member 12 is described in more detail below. The rotational or angular position of the dose follower 12 with respect to the housing 2 may be indicative of the size of the dose which is currently set. Accordingly, the movable member 12 can be used to indicate the size of the set dose. For this purpose dose indicia can be provided on an outer surface of the movable member and a window (not illustrated) could be provided in the housing 2 to enable that the user can view the relevant indicia which indicates the currently set dose. In this case, the movable member acts as dose indication member. Alternatively, the movable member 12 can be operatively coupled to a separate dose indication member which is driven by the rotational movement of the movable member relative to the housing and configured to indicate the currently set dose.

A biasing member 13 is provided. The biasing member 13 is provided to define a specific angular position of the dose setting member 11 relative to the movable member 12. This position is a regular or locking position between the dose setting member 11 and the dose follower or movable member 12 as will be discussed further below. Consequently, if there is relative rotation between the movable member and the dose setting member in either rotational direction, the biasing member is biased and tends to restore the initial or locking position between the two members. The biasing member 13 may be a spring, e.g. a torsion spring, seated between and/or fixed to the movable member 12 and the dose setting member 11.

As depicted, the piston rod 8 may extend through the drive member 10, the movable member 12 and/or the dose setting member 11. The dose setting member 11 may be received in the movable member 12.

Furthermore, a mechanical interface 14 is provided. The mechanical interface is expediently provided to rotationally lock the movable member 12 relative to the housing 2 in defined angular positions corresponding to whole-number multiples of the unit increment. Accordingly, the mechanical interface 14 preferably counteracts the force or torque transferred to the movable member 12 via the energy storage member 7, which would, if it were not reacted by the mechanical interface, rotate the movable member 12 in the decrementing direction. Further, the interface 14 permits rotation of the movable member 12, preferably in the incrementing and decrementing direction, whole-number multiples of a unit increment. The mechanical interface 14 can be formed as a ratchet interface.

The mechanical interface 14 may be provided between the movable member 12 and a member of the device which is rotationally secured relative to the housing, preferably at least during dose setting or permanently, or between movable member 12 and housing 2. The rotational lock of the movable member 12 provided by the mechanical interface 14 may be released for driving the dispensing action of the drive mechanism. Accordingly, the mechanical interface 14 may be provided between the movable member 12 and the housing 2 or, as depicted in the exemplary embodiment, between the movable member 12 and the drive member 10. The drive member 10 is releasably rotationally locked relative to the housing. For this purpose, a clutch spring 15 is provided which biases the drive member into a clutch engagement with the housing 2 which prevents rotation of the drive member relative to the housing. Axial movement of the drive member 10 relative to the housing 2 may release the clutched engagement and allow rotational movement of the drive member relative to the housing, e.g. for dispensing the dose. Accordingly, in a dose setting mode of operation of the mechanism, the drive member 10 may be rotationally locked relative to the housing 2 and in a dose dispensing mode of operation of the mechanism, the rotational lock of the drive member 10 relative to the housing 2 may be released. When the lock is released, rotational movement of the movable member caused by the energy stored in the energy storage member 7 may be transferred to the drive member 10. The rotation of the drive member causes distal movement of the piston rod relative to the housing 2.

The mechanical interface 14 may be configured to define the unit increment, i.e. the minimum amount of rotation which is permitted of the movable member 12 relative to the housing 2 and/or the drive member 10. Consequently, the unit increment may correspond to the minimum dose which can be set by the device. The mechanical interface may be a radial ratchet interface. That is to say, a radial relative movement between features establishing the interface may be required to rotate one of the ratchet members (the movable member 12) relative to the other one of the ratchet members (the drive member 10 or housing 2). The radial movement may disengage the ratchet feature of one of the ratchet members from a ratchet feature of the other one of the ratchet members which form the ratchet system.

Elements of the device or the systems described herein which are moving and especially the elements which are rotating in the device or in the systems described herein may be arranged concentrically, particularly with respect to the common rotation axis. The rotation axis is symbolized by the line A in FIG. 1.

In the following, some embodiments of particularly advantageous implementations associated with the mechanical interface are described.

Figure 2:
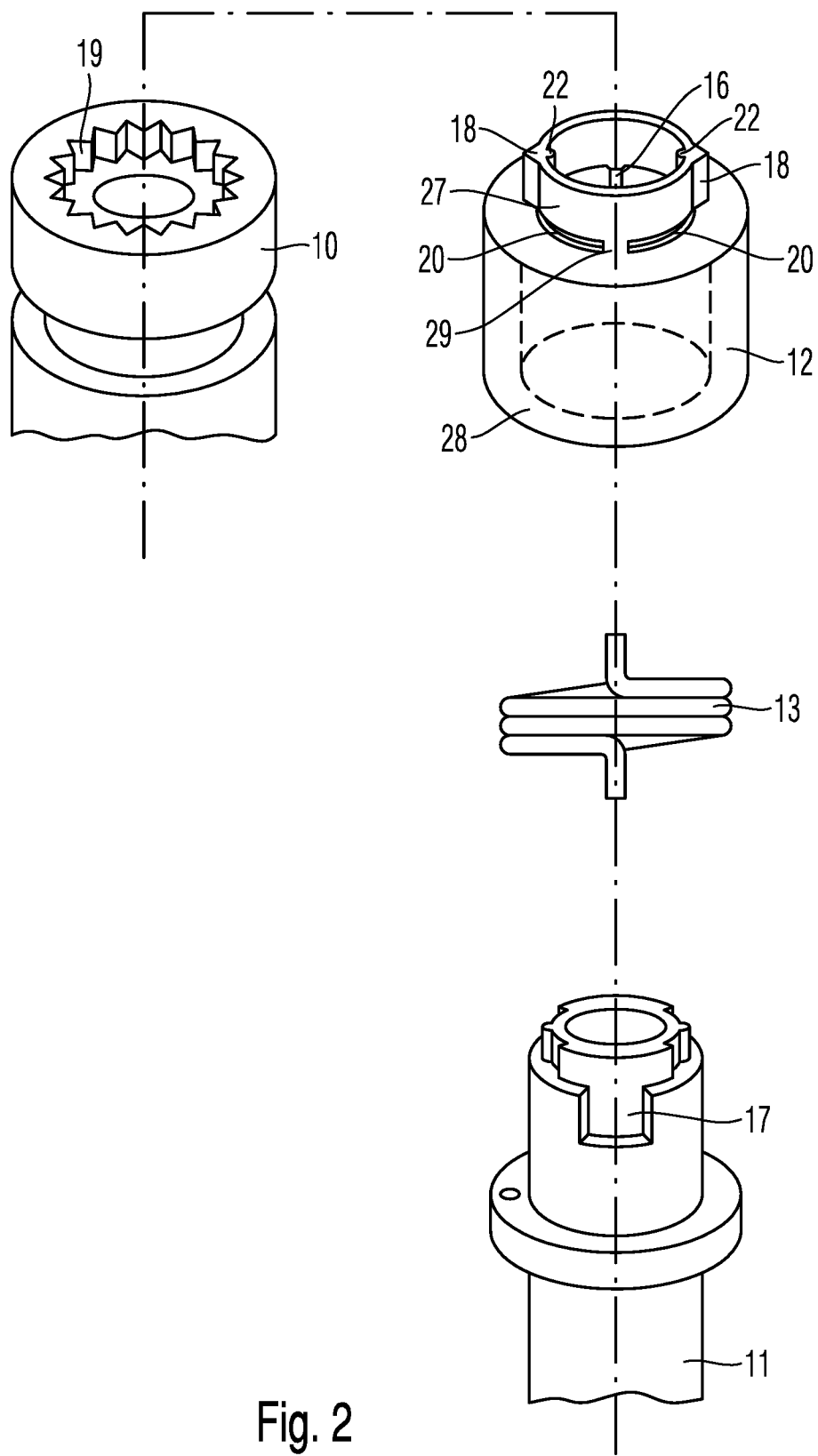

Key members of one implementation of a particularly advantageous system are shown in an exploded view in FIG. 2. The system comprises the dose setting member 11 as a first member. The movable member 12 is provided as a second member. The drive member 10 is provided as a third member. As already explained above, the housing 2 could also act as a third member. Further, the biasing member 13 is shown in FIG. 2. FIG. 3 shows a schematic sectional view of the components shown in FIG. 2 as assembled and, in addition the energy storage member 7. FIG. 4 shows a cross section taken along the line A-A in FIG. 3 and FIG. 5 shows a cross section taken along the line B-B in FIG. 3.

Referrals to the dose setting member 11 herein above and below may be understood as also referring to a general first member. Referrals to the movable member 12 may be understood as also referring to a general second member or first ratchet member. Referrals to a drive member may be understood as also referring to a general third member or second ratchet member, which may be permanently or temporarily rotationally secured relative to another component. The movable member 12 is preferably coupled to the energy storage member such that rotation in the first direction increases the energy stored in the energy storage member and rotation in the opposite second rotational direction decreases the energy. Also incrementing direction and decrementing direction may refer to a general first rotational direction and a general second rotational direction, respectively.

FIG. 4 illustrates the dead-angle follower coupling between the dose setting member 11 and the movable member 12. The coupling is formed by means of a protrusion 16. The protrusion 16 extends in the radial direction. In the depicted embodiment, the protrusion is provided on the movable member 12 and/or extends in the radial inward direction as seen from the movable member 12. However, it is immediately apparent that the protrusion need not be provided on the movable member 12 but could also be provided on the dose setting member 11. The general functionality of the coupling would not be affected by doing so. The other element of the coupling is formed by an indentation 17. The protrusion 16 is received within the indentation 17, in particular radially. As is apparent from FIG. 4, a plurality of protrusion and indentation pairs, e.g. two pairs, are provided. The protrusions and indentations of different pairs may be aligned as seen in the radial direction.

One angular face—that is to say, a surface which delimits an element in the angular or rotational direction—of the protrusion is arranged to abut one angular face of the indentation in either rotational direction. Accordingly, after a clearance 26 shown in FIG. 4 has been closed between the dose setting member 11 and the movable member 12, the dose setting member carries the movable member 12 with it, for example to increase or decrease the size of a set dose or decrease the size of the dose. The position depicted in FIG. 4 may be the one defined by the biasing member 13, i.e. the initial position or locking position of the dose setting member 11. As depicted, rotational movement of the dose setting member 11 relative to the movable member 12 is possible in both rotational directions by a dead-angle which is defined by the angular extension of the clearance 26. The dead-angles may be equal in both rotational directions or different. If they are different, the dead-angle in the incrementing direction may be less than or greater than the dead angle in the decrementing direction. Although the member 12 may be under the bias of the energy storage member 7, this bias is not transferred to the dose setting member 11 via the coupling but rather is compensated or reacted by means of the mechanical interface which is described later on. The angular clearance 26 between the dose setting member 11 and the movable member 12 may be less than the angle corresponding to two unit increments, to one unit increment or to one half of one unit increment. The dead-angle follower coupling may be provided by features (protrusion and indentation) arranged in a distal section of the dose setting member.

FIG. 5 illustrates the mechanical interface between the drive member 10, or the housing 2 as the case may be, and the movable member 12. The mechanical interface 14 is formed by the cooperation of at least one first interface feature 18 (first ratchet feature) and at least one second interface feature 19 (second ratchet feature). The respective interface feature may be a protrusion or tooth. The respective feature is oriented radially. As is apparent from FIG. 5, the movable member is arranged between the drive member 10 and the dose setting member 11 as seen in a sectional view. The respective interface feature extends in the radial direction.

The mechanical interface is a radial ratchet interface which is formed by angular faces of the associated interface features abutting and preventing expediently that the movable member 12 rotates relative to the drive member 10 unless a torque is applied which exceeds the maximum torque which the interface 14 is designed to react. If the torque transferred via the movable member to the mechanical interface is increased beyond this maximum torque, the torque can no longer be reacted by the interface. Then, the movable member is rotated relative to the drive member 10. During this rotation, the interface feature 18 is radially displaced, disengages the interface feature 19 and is brought into engagement with the subsequent interface feature 19. Expediently, the interface is designed so as to react all torques occurring during the regular operation of the system. If the system is a drug delivery device, the maximum torque may be the one transferred by an energy storage member to the interface when a maximum settable dose has been set to be delivered from the device. In the depicted embodiment, the distance between two adjacent interface features 19 defines the unit increment, that is to say the minimum angle distance by which the movable member has to be rotated to be in a stable position again. The torque which can be reacted by the interface 14 can be set by the steepness of the angular faces which block the rotation of the movable member. The less the face is inclined relative to the radial direction, the higher the maximum torque. Two oppositely disposed interface features are provided to engage the continuous toothing formed by the interface features 19. In the depicted embodiment, the angle corresponding to one unit increment is 20° as 18 stable positions—each corresponding to a pocket defined between two adjacent interface features 19—are defined. Clearly other subdivisions are possible. The maximum settable dose may require a rotation of the dose setting member by more the 720°.

As is apparent from the FIG. 2, the first interface feature 18 is provided in an interface section 27 of the movable member 12. The interface section 27 is connected to a body 28 of the movable member 12. The interface section is designed to be elastically deformable. This allows a radial movement of the interface feature 18 relative to the interface feature 19 in order to enable rotation of the movable member 12 relative to the drive member 10 or the housing 2 in the relevant direction. The body 28 is designed to be rigid. The body 28 may be rigidly coupled to the interface section 27 via webs 29. A cutout 20 may be provided in the movable member 12 to provide (radial) resiliency for the first interface feature 18. The interface section may have a reduced diameter and/or wall thickness as compared to the body 28. This facilitates reception of the section within the region of the drive member 10 which has the interface feature 19.

For rotating the movable member 12 relative to the drive member 10, the first interface feature 18 has to be moved radially, in the depicted embodiment in the inward direction, while in abutment with the slanted angular face of the interface feature 19, until it can relax and rest in the next ratchet pocket defined between two adjacent interface features 19. In the situation depicted in FIG. 4 and FIG. 5, the dose setting member 11 is in the locking position. In this position, radial movement of the interface feature 18 is prevented. Accordingly, disengagement of the first interface feature and the second interface feature is prevented. Thus, the movable member cannot rotate in either rotational direction as the required disengagement for releasing the rotational lock provided by the interface 14 is prevented. The dose setting member 11 comprises a protrusion 21 or a locking feature, e.g. two oppositely disposed locking features 21. The locking features extend towards the moveable member 12, e.g. radially and/or outwardly. The locking feature 21 is radially oriented. A radial end face of the locking feature 21 faces the movable member and, preferably a protrusion 22 which protrudes from the movable member 12 in the direction of the dose setting member 11. Feature 21 and protrusion 22 may be angularly aligned. The locking feature 21 and/or the protrusion 22 may be angularly aligned with or overlap with the first interface feature 18. However, other implementations, such as involving an angular offset, are also possible. The illustrated arrangement, however, may provide the most efficient configuration as the interface feature 18 is supported radially at its angular position.

As shown in FIG. 5, a limited radial movement in that direction which would be required for disengaging the interface features 18 and 19 is allowed as there is a radial clearance 30 between the locking feature 21 and the movable member 12, in particular between the locking feature 21 and the protrusion 22. However, the radial movement permitted by the clearance 30 is less than the radial movement required for allowing a rotation of the movable member 12 relative to the drive member 10. Thus, in the locking position illustrated in FIG. 5, the interface 14 cannot be disengaged unintentionally, for example if a drug delivery device is dropped on the floor when a dose has been set already. Thus, it is prevented that energy in the energy storage member is released without intention. User safety is increased in this way.

The protrusion 22 and/or the locking feature 21 may have an angular dimension or extension which decreases towards their free (radial) end. Locking feature 21 and protrusion 22 may be formed alike and face one another. In the region angularly adjoining the locking feature 21, a recess 31 may be formed, expediently on one or on both sides of the locking feature 21. The angular extension of the respective recess is, preferably greater than or equal to the angular clearance between the protrusion 16 and the angular face of the indentation 17 depicted in FIG. 4. Accordingly, the recess provides room for a radial movement and may receive the protrusion 22 when the movable member rotates once the dose setting member 11 has been rotated by the deadangle in either rotational direction.

FIG. 6 shows a more detailed representation of FIG. 3. FIGS. 7 and 8 do illustrate the situation when, starting from the locking position illustrated in FIGS. 4 and 5, the dose setting member 11 is rotated relative to the movable member 12, for example in the anti-clockwise direction. Typically, the anti-clockwise direction is the direction to decrease the size of a previously set dose. However, it is readily apparent that the increasing of the dose may be performed in an analogue way by rotation in the opposite direction. As shown, the angular side faces of the indentation and the protrusion 16 abut such that further rotation of the dose setting member is transferred to the movable member 12. Also, the locking feature 21 has been rotated away from the locking position and/or the protrusion 22. Accordingly, as a radial movement between interface features 18 and 19 is no longer blocked, the mechanical interface 14 can be disengaged and the movable member 12 can be rotated relative to the drive member 10 to increment or decrement the movable member 12. Thus, if, starting from the situation shown in FIGS. 7 and 8, the dose setting member is rotated further, the interface feature 18 may move radially, e.g. inwardly, and engage the next interface feature 19 which provides a stable rotational position. As is apparent from FIG. 8, it is preferred that the mechanical interface is strong enough to counteract every torque transferred to it via the energy storage member during regular operation.

The interface features may be symmetric (as depicted) or asymmetric, particularly in section taken along a plane perpendicular to the axis. Symmetric features guarantee that the force or torque required to rotate the movable member 12 is equal in both directions. Asymmetric ratchet features may require greater forces or torque to rotate the movable member in one direction as compared to the opposite direction. In the present instance, if an asymmetric interface should be provided, the interface features will expediently be configured to require a greater force or torque which has to be applied to rotate the movable member 12 in that direction in which the energy storage member 7 tends to rotate the movable member 12.

When the desired dose has been set, the button 25 may be pressed in the distal direction. This causes distal movement of the drive member 10 relative to the housing 2, preferably via the dose setting member 11 which follows distal movement of the button 25. The distal movement disengages the drive member 10 from the housing 2 and, preferably, rotationally locks the drive member 10 and the movable member 12, e.g. be engaging a splined coupling between the drive member and the movable member 12. As the torque of the energy storage member 12 is no longer reacted, the movable member 12 rotates as does the drive member. The rotation of the drive member 10 causes the piston rod 8 to be displaced distally relative to the housing 2. During dose delivery, the dose setting member 11 may or may not rotate relative to the button 25.

In the implementation of the mechanical interface 14 illustrated in FIGS. 5 through 8, the interface features 19 which define the unit increment are circumferentially disposed uniformly over the entire circumference, i.e. 360°. However, there are also other implementations of ratchet system which are suitable in the disclosed concept. Such implementations are described in the following, where the focus is on the differences to the interface described above. Thus, features described above may also apply for the following description.

Figure 11:
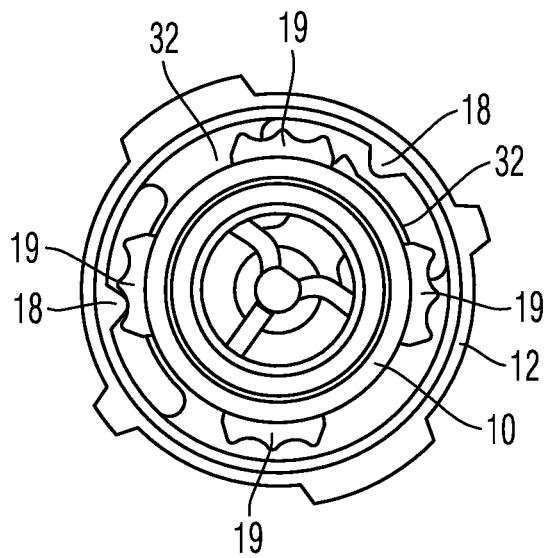
Figure 12:
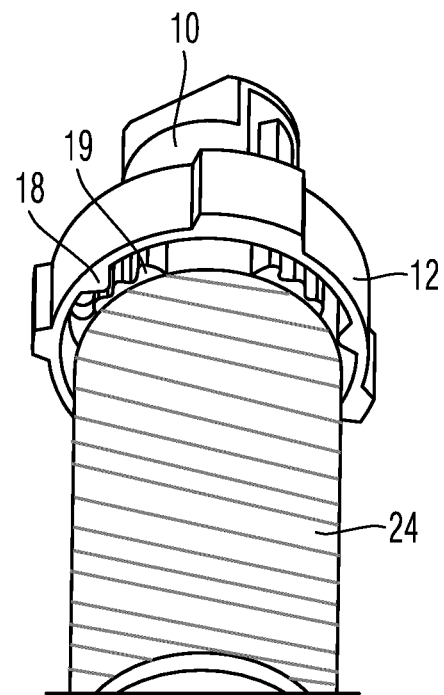

FIGS. 9 through 12 illustrate further implementations of a mechanical interface 14 between the movable member 12 and the drive member 10 or the housing 2 respectively. FIG. 9 shows a small section of the device of FIG. 1. FIG. 10 illustrates an embodiment of an implementation on the basis of a sectional view and FIGS. 11 and 12 illustrate another embodiment on the basis of a perspective view. The mechanical interface 14 is still designed such that the movable member 12 is rotatable in both rotational directions relative to the drive member 10 or housing 2 in wholenumber multiples of a unit increment only. The unit increment is defined by an arrangement of interface features 19 which are circumferentially disposed and arranged at a distance from one another corresponding to a unit increment. However, the interface features do not extend over the entire circumference as in FIG. 5. Rather, there is an angular gap 32 present which separates adjacent interface features. The angular extension of the gap 32 may be greater than the angle corresponding to one unit increment, e.g. greater than or equal to an angle corresponding to the following number of unit increments: 2, 3, 4, 5, 6, 7, 8, 9, 10.

As depicted in FIG. 10 the interface features 19 do only extend over a smaller angular range of, e.g. 180°. Accordingly, another angular range, i.e. the gap 32, is free of interface features. The range may be 360° minus the angular extension of the interface features. Nevertheless, the mechanical interface is still configured to perform rotational movements only in multiples of one unit increment. For doing so, a plurality of first interface features 18 is provided. In the embodiment shown in FIG. 10, two interface features 18 are provided. The minimum number of interface features 18 which are provided to cooperate with interface features 19 to establish a rotational locking of the movable member 12 relative to the drive member 10 is 360° divided by the sum of all angular distances which are not provided with interface features 19 which define the unit increment. In the embodiment of FIG. 10 this minimum is two as the angular extension of the interface features 19 is 180°.

In the embodiment in FIG. 10, only one angular side face of all interface features 18 interacts in each rotational direction with the teeth defining the second interface features 19, preferably in any stable position defined by the interface 14. Rotation in the clockwise direction is hindered by the side face of interface feature 18a abutting a side face of one interface feature 19. Rotation in the anti-clockwise direction is hindered by the side face of interface feature 18b abutting the side face of one interface feature 19. Consequently, only one interface feature 18 provides the engagement which hinders rotational movement in one specific directions in any stable position defined by the interface 14.

The interface features 19 which define the unit increment may not only be distributed in one contiguous angular region as shown in FIG. 10, but be also distributed angularly more widely. This is shown in FIGS. 11 and 12, where four groups of interface features 19 are shown, the groups being angularly separated by gaps 32 which are greater than one unit increment, specifically greater than or equal to the angle corresponding to three unit increments or four unit increments. Within each group, the interface features 19 are arranged at a distance which corresponds to one unit increment. In FIG. 11 it is ensured as well that only one interface feature 18 interacts with all of the groups to hinder rotation in each rotational direction. In FIG. 11, as opposed to FIG. 10, the radial orientation of interface features 18 and 19 is reversed.

It is advantageous that only one pair of interface features 18 and 19 provides a rotational lock in a specific rotational direction as only one abutment or engagement has to be released to achieve rotational movement in the relevant direction. This provides confidence for the user and, in particular, avoids that the user may misinterpret two different disengagement feedbacks which might be generated at slightly offset times during the rotation process as indicating that the device is not functioning properly.

Further, as not the entire circumference is covered with interface features or teeth, the gap 32 can be used to guide an additional element through this region, for example to engage with a thread provided axially offset from the interface features 19. Such a thread 24 is depicted in FIG. 12. The additional element may be a last dose nut, which is configured to prevent that a dose is set which exceeds the quantity of drug available in the reservoir. The last dose nut may be coupled to the dose setting member 11 during dose setting and uncoupled from the setting member 11 during dose dispense. Thus, the axial position of the nut on the thread may correspond to the entire quantity of drug which has already been dispensed from the reservoir.

As the interface 14 is loaded unsymmetrically, as only one interface feature pair 18/19 carries the load in the respective rotational direction, an alignment feature 23 may be provided which maintains the movable member 12 and the drive member 10 in proposer axial alignment. The alignment feature is depicted in FIG. 9, for example. This alignment feature may guide the body 28 axially. It may be realized by a section of the drive member 10 extending around the outer surface of the body 28. Other configurations are possible as well, of course.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS 1 drug delivery device
2 housing
3 reservoir
4 drug
5 bung
6 septum
7 energy storage member
8 nut section
10 drive member
11 dose setting member
12 dose follower
13 biasing member
14 mechanical interface
15 clutch spring
16 protrusion
17 indentation
18 first interface feature
18a interface feature
18b interface feature
19 second interface feature
20 cut-out
21 locking feature
22 protrusion
23 alignment feature
24 thread
25 button
26 clearance
27 interface section
28 body
29 web
30 clearance
31 recess
32 gap
A Axis

The invention claimed is:
1. A system, comprising:
a first member, a second member, and a third member,
wherein the first member and the second member are rotatable relative to the third member,
wherein the first member and the second member are coupled to one another by a dead-angle follower coupling, wherein the dead-angle follower coupling is configured such that the first member and the second member are rotatable relative to one another but only within a limited angular range,
wherein the second member and the third member are rotationally coupled to one another by a switchable coupling mechanism, wherein the switchable coupling mechanism is switchable between two different states, a locked state and a non-locked state, wherein the maximum torque transferable between the second member and the third member via the switchable coupling mechanism in the locked state is greater than in the non-locked state, wherein the switchable coupling mechanism is configured such that the switchable coupling mechanism is in the locked state when the first member is in a locking position relative to the second member, the locking position being within the limited angular range, and wherein the locking position is chosen such that, starting from the locking position, the first member is rotatable relative to the second member by a first dead-angle in a first rotational direction to switch the coupling mechanism to the non-locked state and by a second dead-angle in a second rotational direction opposite to the first rotational direction to switch the coupling mechanism to the non-locked state.

2. The system of claim 1, wherein the system is configured such that, after a relative rotation by the first dead-angle or the second dead-angle has been performed starting from the locking position, the first member and the second member are rotationally locked in the first rotational direction or in the second rotational direction, respectively.

3. The system of claim 1, wherein the second member and the third member are coupled to one another by a mechanical interface that is configured to define stable, relative angular positions between the second member and the third member only in whole-number multiples of a unit increment, wherein the mechanical interface is formed by at least one second member interface feature of the second member and at least one third member interface feature of the third member which engage one another in each relative angular position, and wherein the dead-angle follower coupling is further configured to cause the first dead-angle and/or the second dead-angle to be greater than or equal to half of the unit increment.

4. The system of claim 3, wherein the switchable coupling mechanism comprises the mechanical interface and a locking feature associated with the first member, and wherein the locking feature is arranged to prevent disengagement of the at least one second and third member interface features (18, 19) in the locking position.

5. The system of claim 4, wherein, when the first member is in the locking position, the locking feature is arranged to allow a limited radial movement between the at least one second and third member interface features, but only to an extent which is insufficient to rotate the second member by one unit increment relative to the third member.

6. The system of claim 3, wherein the second member comprises a plurality of second member interface features that are distributed circumferentially, wherein the angular distance between at least two adjacent second member interface features is greater than an angle corresponding to one unit increment, and wherein the third member comprises a plurality of third member interface features that are distributed circumferentially, wherein the angular distance between at least two adjacent third member interface features is greater than the angle corresponding to one unit increment, wherein the system is configured such that, in any relative angular position defined by the mechanical interface, an angular face of only one third member interface feature interacts with an angular face of only one second member interface feature in order to prevent relative rotational movement between the second member and the third member in the first rotational direction and in the second rotational direction.

7. The system of claim 6, wherein the second member interface features and/or the third member interface features are grouped into one or more groups, and wherein in each group, adjacent interface features are separated by an angle corresponding to one unit increment.

8. The system of claim 7, wherein two adjacent groups are separated by an angle corresponding to more than one unit increment.

9. The system of claim 3, further comprising an energy storage member, wherein the second member is coupled to the energy storage member, wherein rotation of the second member in the first rotational direction relative to the third member increases energy stored in the energy storage member and wherein the energy stored in the energy storage member tends to rotate the second member in the second rotational direction opposite to the first rotational direction.

10. The system of claim 9, wherein the mechanical interface between the second member and the third member is capable of reacting torque transferred to the second member from the energy storage member in the non-locked state.

11. The system of claim 9, wherein the first rotational direction is an incrementing direction, and wherein the second rotational direction is a decrementing direction.

12. The system of claim 1, further comprising a biasing mechanism that is configured to exert a force which tends to move the first member into the locking position relative to the second member when the first member has been displaced away from the locking position in either of the first rotational direction or the second rotational direction relative to the second member.

13. The system of claim 1, wherein the rotational coupling between the second member and the third member provided by the coupling mechanism can be released by a relative axial movement between the second member and the third member.

14. The system of claim 13, wherein when the rotational coupling has been released, the second member and the third member are rotationally locked to one another such that rotational movement of the second member is transferred to the third member.

15. The system of claim 14, wherein when the rotational coupling has been released, the second member and the third member are rotationally locked to one another by a splined connection.

16. The system of claim 1, wherein the dead-angle follower coupling is further configured to have the first dead-angle and/or the second dead-angle being greater than or equal to at least one of 1°, 2°, 3°, 4°, 5°, and 10°.

17. A drug delivery device comprising:
a system comprising:
a first member, a second member, and a third member,
wherein the first member and the second member are rotatable relative to the third member,
wherein the first member and the second member are coupled to one another by a dead-angle follower coupling, wherein the dead-angle follower coupling is configured such that the first member and the second member are rotatable relative to one another but only within a limited angular range,
wherein the second member and the third member are rotationally coupled to one another by a switchable coupling mechanism, wherein the switchable coupling mechanism is switchable between two different states, a locked state and a non-locked state, wherein the maximum torque transferable between the second member and the third member via the switchable coupling mechanism in the locked state is greater than in the non-locked state, wherein the switchable coupling mechanism is configured such that the switchable coupling mechanism is in the locked state when the first member is in a locking position relative to the second member, the locking position being within the limited angular range, and wherein the locking position is chosen such that, starting from the locking position, the first member is rotatable relative to the second member by a first dead-angle in a first rotational direction to switch the coupling mechanism to the non-locked state and by a second dead-angle in a second rotational direction opposite to the first rotational direction to switch the coupling mechanism to the non-locked state; and a reservoir comprising a drug.

18. The drug delivery device of claim 17, wherein the system is configured such that, after a relative rotation by the first dead-angle or the second dead-angle has been performed starting from the locking position, the first member and the second member are rotationally locked in the first rotational direction or in the second rotational direction, respectively.

19. The drug delivery device of claim 17, wherein the system further comprises a biasing mechanism that is configured to exert a force which tends to move the first member into the locking position relative to the second member when the first member has been displaced away from the locking position in either of the first rotational direction or the second rotational direction relative to the second member.

20. The drug delivery device of claim 17, wherein the dead-angle follower coupling is further configured to have the first dead-angle and/or the second dead-angle being greater than or equal to at least one of 1°, 2°, 3°, 4°, 5°, and 10°.

* * * * *

UNITED STATES PATENT AND TRADEMARK OFFICE
CERTIFICATE OF CORRECTION

| | |
|---|---|
| PATENT NO. | : 11,565,052 B2 |
| APPLICATION NO. | : 16/766204 |
| DATED | : January 31, 2023 |
| INVENTOR(S) | : Ralph Donald Quentin Collings et al. |

It is certified that error appears in the above-identified patent and that said Letters Patent is hereby corrected as shown below:

In the Claims

In Column 25, Lines 41-42, Claim 4, after "features" delete "(18, 19)"

In Column 26, Lines 15-17, Claim 9, delete "member" and insert -- member, --

Signed and Sealed this
Sixteenth Day of May, 2023

Katherine Kelly Vidal
*Director of the United States Patent and Trademark Office*